United States Patent [19]
Li et al.

[11] Patent Number: 6,060,272
[45] Date of Patent: May 9, 2000

[54] HUMAN G-PROTEIN COUPLED RECEPTORS

[75] Inventors: Yi Li, Sunnyvale, Calif.; Steven M. Ruben, Olney, Md.

[73] Assignee: Human Genome Sciences, Inc., Rockville, Md.

[21] Appl. No.: 08/852,824

[22] Filed: May 7, 1997

[51] Int. Cl.$^7$ .......................... C07H 21/04; C12N 15/12; C12N 15/63

[52] U.S. Cl. ................... 435/69.1; 536/23.1; 536/24.31; 435/320.1; 435/325; 435/253.3; 435/172.3; 435/235.1

[58] Field of Search .............................. 435/69.1, 320.1, 435/325, 252.3, 172.3, 253.3, 253.1; 536/23.1, 24.31

[56] References Cited

U.S. PATENT DOCUMENTS

| | | | |
|---|---|---|---|
| 5,585,476 | 12/1996 | MacLennan et al. | 536/23.5 |
| 5,834,587 | 11/1998 | Chan et al. | 530/324 |
| 5,912,144 | 6/1999 | Young et al. | 435/69.1 |

FOREIGN PATENT DOCUMENTS

| | | |
|---|---|---|
| 9412519 | 6/1994 | WIPO . |
| WO 98/48016 | 10/1998 | WIPO . |

OTHER PUBLICATIONS

EMBL Accession No. D81412 (Feb. 7, 1996).
EMBL Accession No. g2875724 (Feb. 16, 1998).
EMBL Accession No. AA447306 (Apr. 7, 1998).
Nelson et al. (1998) Genomics 47(1):12–25.
Lin, C. C. et al., Differential Fluorescent Staining of Human Chromosomes with Daunomycin and Adriamycin–The D—Bands, Science, vol. 190, pp. 61–63, 1975.
NCBI Entrez, GenBank Accession No. D81412, Fujiwara, T. et al. (Feb. 1996).
NCBI Entrez, GenBank Accession No. AA274112, Marra, M. et al. (Mar. 1997).
NCBI Entrez, GenBank Accession No. AA353166, Adams, M.D. et al. (Apr. 1997).
NCBI Entrez, GenBank Accession No. AA810452, NCI–CGAP (1998).
NCBI Entrez, GenBank Accession No. AA447306, Nelson, P.S. et al. (1998).
NCBI Entrez, GenBank Accession No. AJ000479, Graeler, M.H. et al. (1998).
NCBI Entrez, GenBank Accession No. CAA04118, Graeler, M.H. et al. (1998).
NCBI Entrez, GenBank Accession No. CAA06847, Graeler, M.H. et al. (1998).

*Primary Examiner*—Elizabeth Kemmerer
*Assistant Examiner*—Nirmal S. Basi
*Attorney, Agent, or Firm*—Sterne, Kessler, Goldstein & Fox P.L.L.C.

[57] ABSTRACT

Two human G-protein coupled receptor polypeptides and DNA (RNA) encoding each of such polypeptides and a procedure for producing such polypeptides by recombinant techniques is disclosed. Also disclosed are methods for utilizing such polypeptides for identifying antagonists and agonists to such polypeptides. Also disclosed are diagnostic methods for detecting a mutation in the nucleic acid sequence of each of the G-protein coupled receptors.

21 Claims, 7 Drawing Sheets

```
  1 GCACGAGGAACAGAACACTTTCTCATGTCCAGGGTCAGATTACAAGAGCACTCAAGACTT   60

61 TACTGACGAAAACTCAGGAAATCCTCTATCACAAAGAGGTTTGGCAACTAAACTAAGACA  120

121 TTAAAAGGAAAATACCAGATGCCACTCTGCAGGCTGCAATAACTACTACTTACTGGATAC  180

181 ATTCAAACCCTCCAGAATCAACAGTTATCAGGTAACCAACAAGAAATGCAAGCCGTCGAC  240
  1                                                   M Q A V D    5

241 AATCTCACCTCTGCGCCTGGGAACACCAGTCTGTGCACCAGAGACTACAAAATCACCCAG  300
  6  N L T S A P G N T S L C T R D Y K I T Q                       25

301 GTCCTCTTCCCACTGCTCTACACTGTCCTGTTTTTTGTTGGACTTATCACAAATGGCCTG  360
 26  V L F P L L Y T V L F F V G L I T N G L                       45

361 GCGATGAGGATTTTCTTTCAAATCCGGAGTAAATCAAACTTTATTATTTTTCTTAAGAAC  420
 46  A M R I F F Q I R S K S N F I I F L K N                       65

421 ACAGTCATTTCTGATCTTCTCATGATTCTGACTTTTCCATTCAAAATTCTTAGTGATGCC  480
 66  T V I S D L L M I L T F P F K I L S D A                       85

481 AAACTGGGAACAGGACCACTGAGAACTTTTGTGTGTCAAGTTACCTCCGTCATATTTTAT  540
 86  K L G T G P L R T F V C Q V T S V I F Y                      105

541 TTCACAATGTATATCAGTATTTCATTCCTGGGACTGATAACTATCGATCGCTACCAGAAG  600
106  F T M Y I S I S F L G L I T I D R Y Q K                      125

601 AcCACCAGGCCATTTAAAACATCCAACCCCAAAAATCTCTTGGGGGCTAAGATTCTCTCT  660
126  T T R P F K T S N P K N L L G A K I L S                      145

661 GTTGTCATCTGGGCATTCATGTTCTTACTCTCTTtGCCTAACATGATTCTGACCAACAGg  720
146  V V I W A F M F L L S L P N M I L T N R                      165

721 CAGCCGAGAGACAAGAATGTGaAGAAaTGCTCTTTCCTTAAATCAGAGTTCGGTCTAGTC  780
166  Q P R D K N V K K C S F L K S E F G L V                      185

781 TGGCATGAAATAGTAAATTACATCTGTCAAGTCATTTTCTGGATTAATTTCTTAATTGTT  840
186  W H E I V N Y I C Q V I F W I N F L I V                      205
```

FIG.1A

```
841  ATTGTATGTTATACACTCATTACAAAAGAACTGTACCGGTCATACGTAAGAACGAGGGGT  900
206   I  V  C  Y  T  L  I  T  K  E  L  Y  R  S  Y  V  R  T  R  G   225

901  GTAGGTAAAGTCCCCAGGAAAAAGGTGAACGTCAAAGTTTTCATTATCATTGCTGTATTC  960
226   V  G  K  V  P  R  K  K  V  N  V  K  V  F  I  I  I  A  V  F   245

961  TTTATTTGTTTTGTTCCTTTCCATTTTGCCCGAATTCCTTACACCCTGAGCCAAACCCGG  1020
246   F  I  C  F  V  P  F  H  F  A  R  I  P  Y  T  L  S  Q  T  R   265

1021 GATGTCTTTGACTGCACtGcTGAAAATACTCTGTTCTATGTGAAAGAGAGCACTCTGTGG  1080
266   D  V  F  D  C  T  A  E  N  T  L  F  Y  V  K  E  S  T  L  W   285

1081 TTAACTTCCTTAAATGCATGCCTGGATCCGTTCATCTATTTTTTCCTTTGCAAGTCCTTC  1140
286   L  T  S  L  N  A  C  L  D  P  F  I  Y  F  F  L  C  K  S  F   305

1141 AGAAATTCCTTGATAAGTATGCTGAAGTGCCCCAATTCTGCAACATCTCTGTCCCAGGAC  1200
306   R  N  S  L  I  S  M  L  K  C  P  N  S  A  T  S  L  S  Q  D   325

1201 AATAGGAAAAAAGAACAGGATGGTGGTGAcCCAAATGAAGAGACTCCAATGTAAACAAAT  1260
326   N  R  K  K  E  Q  D  G  G  D  P  N  E  E  T  P  M  *         343

1261 TAACTAAGGAAATATTTCAATCTCTTTGTGTTCAGAACTCGTTAAAGCAAAGCGCTAAGT  1320

1321 AAAAATATTAACTGACGAAGAAGCAACTAAGTTAATAATAATGACTCTAAAGAAACAGAA  1380

1381 GATTACAAAAGCAATTTTCATTTACCTTTCCAGTATGAAAAGCTATCTTAAAATATAGAA  1440

1441 AACTAATCTAAACTGTAGCTGTATTAGCAGCAAAACAAACGACATCCAATTGTCATGCTG  1500

1501 CATGCAAAACTACACAGAATTCATGTTTTGgCAGAGTTTTGGCAAAATGAGTAATCATAT  1560

1561 AATATTTACTGTAATTTTTAAAATACATTATCGTTCACAATTTTATTTTTTCATAATCAA  1620

1621 CTAAGGAAGAACGATCAATTGGATATAATCTTCTTACCAAAAATGATAGTTAAAATGTAT  1680

1681 ATATATCCTAGTCCCCTAACCaAATCCTGACCTATTGGGATACTTATAAAAATTTAAGTA  1740

1741 AGTGGGATACACAAAGAATAATAACTATTAACTTTTCATTATTAGCcAAAAACCTAAGGG  1800
```

FIG. 1B

1801  ATTTAAACTAATTGAAaCTGTATTTGATTGGACTTAATTTTTTATGTTTATTTAGAAGAT  1860

1861  AAAGATTTAAGAAGACCTTTACAATAAAGAGAAGAAATATCGAAGTCATTAAAATAAGGA  1920

1921  GACTTACTTTTATGACATTCTAATACTAAAAAATATAGAAATATTTCCTTAATTCTAGAG  1980

1981  AAACTAGTTTTACTAATTTTTTACAACTTCAATAATACCATCACTGACACTTACCTTTAT  2040

2041  TAATTAGCTTCTAGAAAATAGCTGCTAATTAGGTTAATGAACATTTTACCTTAGTGAAAA  2100

2101  AAAaTTAATTAAATATGATTACAAAGTTGCACAGCATAACTACTGAGAGGAAAGTGATTG  2160

2161  ATCTGTTTGTAATTACTTGTTTGTATTGGTGTGTATAAAATACAAATTTACATTAAACTC  2220

2221  TAAAtcattaaaAAAAAAAAAAAAAAAA 2247

FIG. 1C

```
  1 MQAVDNLTSAP....GNTSLCTRDYKITQVLFPLLYTVLFFVGLITNGLA  46
    :| .:|:|.:.     ||.:      .......:::|| |.::|::||:.| ||
  3 IQMANNFTPPSATPQGNDCDLYAHHSTARIVMPLHYSLVFIIGLVGNLLA  52

47 MRIFFQIRSKSN.FIIFLKNTVISDLLMILTFPFKILSDAKLGTGPLRTF  95
    : ::.| |.| |  .:: .| ||||:|:.  .:| :|    |. . .: .
 53 LVVIVQNRKKINSTTLYSTNLVISDILFTTALPTRIAYYAMGFDWRIGDA 102

96 VCQVTSVIFYFTMYISISFLGLITIDRYQKTTRPFKTSNPKNLLGAKILS 145
    :|.:|.::||:.  |  :::.|:. :.|||:  ..:|::  .. |.:  || ::
103 LCRITALVFYINTYAGVNFMTCLSIDRFIAVVHPLRYNKIKRIEHAKGVC 152

146 VVIWAFMFLLSLPNMI..LTNRQPRDKNVKKCSFLKSEFGLVWHEIVNYI 193
    :.:|  ::|  .|| :|   :...::     .....:. :... :|.|  :...::
153 IFVWILVFAQTLPLLINPMSKQEAERITCMEYPNFEETKSLPWILLGACF 202

194 CQVIFWINFLIVIVCYTLITKELYRSYVRTRGVGK...VPRKKVNVKVFII 241
    .. ::     ::|:::||. |. .|:|.   ... .:|  | :| :|. ::||
203 IGYVL..PLIIILICYSQICCKLFRTAKQNPLTEKSGVNKKALNTIILII 250

242 IAVFFICFVPFHFARIPYTLSQTR..DVFDCTAENTLFYVKESTLWLTSL 289
    : ||.:||.|:|.| |.. :..  |   :.::|..  :.: .  |: |  .:
251 V.VFVLCFTPYHVAIIQHMIKKLRFSNFLECSQRHSFQISLHFTVCLMNF 299

290 NACLDPFIYFFLCKSFRNSLISMLKCPNSATSLSQDNRKKEQDGGDPNEE 339
    |.|:|||||||  ||:::..::.|||  .  |  .|:|  .  :. .::..:  . .|
300 NCCMDPFIYFFACKGYKRKVMRMLKRQVS.VSISSAVKSAPEENSREMTE 348

340 TPM 342
    |.|
349 TQM 351
```

FIG.2

```
1    GGCACGAGCCCACCCTGCGTCGGGCCTCAGTCAGCCCCCGGGGGAGGCCATGAACGCCAC   60
1                                                        M  N  A  T    4

61   GGGGACCCCGGTGGCCCCCGAGTCCTGCCAACAGCTGGCGGCCGGCGGGCACAGCCGGCT   120
5     G  T  P  V  A  P  E  S  C  Q  Q  L  A  A  G  G  H  S  R  L   24

121  CATTGTTCTGCACTACAACCACTCGGGCCGGCTGGCCGGGCGCGGGGGGCCGGAGGATGG   180
25    I  V  L  H  Y  N  H  S  G  R  L  A  G  R  G  G  P  E  D  G   44

181  CGGCCTGGGGGCCCTGCGGGGGCTGTCGGTGGCCGCCAGCTGCCTGGTGGTGCTGGAGAA   240
45    G  L  G  A  L  R  G  L  S  V  A  A  S  C  L  V  V  L  E  N   64

241  CTTGCTGGTGCTGGCGGCCATCACCAGCCACATGCGGTCGCAACGCTGGGTCTACTATTG   300
65    L  L  V  L  A  A  I  T  S  H  M  R  S  Q  R  W  V  Y  Y  C   84

301  CCTGGTGAACATTACGATGAGTGACCTGCTCACGGGCGCGGCCTACCTGGCCAACGTGCT   360
85    L  V  N  I  T  M  S  D  L  L  T  G  A  A  Y  L  A  N  V  L   104

361  GCTGTCGGGGGCCCGCACCTTCCGTCTGGCGCCCGCCCAGTGGTTCCTACGGAAGGGCCT   420
105   L  S  G  A  R  T  F  R  L  A  P  A  Q  W  F  L  R  K  G  L   124

421  GCTCTTCACCGCCCTGGCCGCCTCCACCTTCAGCCTGCTCTTCACTGCAGGGTTGCGCTT   480
125   L  F  T  A  L  A  A  S  T  F  S  L  L  F  T  A  G  L  R  F   144

481  TGCCACCATGGTGCGGCCGGTGGCCGAGAGCGGGGCCACCAAGACCAGCCGCGTCTACGG   540
145   A  T  M  V  R  P  V  A  E  S  G  A  T  K  T  S  R  V  Y  G   164

541  CTTCATCGGCCTCTGCTGGCTGCTGGCCGCGCTGCTGGGGATGCTGCCTTTGCTGGGCTG   600
165   F  I  G  L  C  W  L  L  A  A  L  L  G  M  L  P  L  L  G  W   184

601  GAACTGCCTGTGCGCCTTTGACCGCTGCTCCAGCCTTCTGCCCCTCTACTCCAAGCGCTA   660
185   N  C  L  C  A  F  D  R  C  S  S  L  L  P  L  Y  S  K  R  Y   204

661  CATCCTCTTCTGCCTGGTGATCTTCGCCGGCGTCCTGGCCACCATCATGGGCCTCTATGG   720
205   I  L  F  C  L  V  I  F  A  G  V  L  A  T  I  M  G  L  Y  G   224

721  GGCCATCTTCCGCCTGGTGCAGGCCAGCGGGCAGAAGGCCCCACGCCCAGCGGCCCGCCG   780
225   A  I  F  R  L  V  Q  A  S  G  Q  K  A  P  R  P  A  A  R  R   244
```

FIG.3A

```
781  CAAGGCCCGCCGCCTGCTGAAGACGGTGCTGATGATCCTGCTGGCCTTCTTGGTGTGCTG  840
245   K   A   R   R   L   L   K   T   V   L   M   I   L   L   A   F   L   V   C   W  264

841  GGGACCACTCTTCGGGCTGCTGCTGGCCGACGTCTTTGGCTCCAACCTCTGGGCCCAGGA  900
265   G   P   L   F   G   L   L   L   A   D   V   F   G   S   N   L   W   A   Q   E  284

901  GTACCTGCGGGGCATGGACTGGATCCTGGCCCTGGCCGTCCTCAACTCGGCGGTCAACCC  960
285   Y   L   R   G   M   D   W   I   L   A   L   A   V   L   N   S   A   V   N   P  304

961  CATCATCTACTCCTTCCGCAGCAGGGAGGTGTGCAGAGCCGTGCTCAGCTTCCTCTGCTG 1020
305   I   I   Y   S   F   R   S   R   E   V   C   R   A   V   L   S   F   L   C   C  324

1021 CGGGTGTCTCCGGCTGGGCATGCGAGGGCCCGGGGACTGCCTGGCCCGGGCCGTCGAGGC 1080
325   G   C   L   R   L   G   M   R   G   P   G   D   C   L   A   R   A   V   E   A  344

1081 TCACTCCGGAGCTTCCACCACCGACAGCTCTCTGAGGCCAAGGGACAGCTTTCGCGGCTC 1140
345   H   S   G   A   S   T   T   D   S   S   L   R   P   R   D   S   F   R   G   S  364

1141 CCGCTCGCTCAGCTTTCGGATGCGGGAGCCCCTGTCCAGCATCTCCAGCGTGCGGAGCAT 1200
365   R   S   L   S   F   R   M   R   E   P   L   S   S   I   S   S   V   R   S   I  384

1201 CTGAAGTTGCAGTCTTGCGTGTGGATGGTGCAACCACCGGGTGCGTGCCAGGCAGGCCCT 1260
385   *                                                                              385

1261 CCTGGGGTACAGGAAGCTGTGTGCACGCAACCTCGCCCTGTATGGGGAGCAGGGAACGGG 1320

1321 ACAGGCCCCCATGGACTTGCCCGGTGGCCTCTCGGGGCTTCTGACGCCATATGGACTTGC 1380

1381 CCATTGCCTATGGCTCACCCTGGACAAGGAGGCAACCACCCCACCTCCCCGTAGGAGCAG 1440

1441 AGAGCACCCTGGTGTGGGGGCGAGTGGGTTCCCCACAACCCCGCTTCTGTGTGATTCTGG 1500

1501 GGAAGTCCCGGCCCCTCTCTGGGCCTCAGTAGGGCTCCCAGGCTGCAAGGGGTGGACTGT 1560

1561 GGGATGCATGCCCTGGCAACATTGAAGTTCGATCATGGTAAAAAAAAAAAAAAAAAAAAA 1620

1621 AAAAAAAAAAAAAAAAA 1637
```

FIG.3B

```
  1  MNATGTPVAPESCQQLAAGGHSRLIVLHYNHSGRLAGRGGPEDGGLGALR   50
     |.:|:.|:...       :.. .:  :|| |||..|:|. .:::.|: ::    .
  1  MGPTSVPLVKAHRSSVSDYVNYDIIVRHYNYTGKLNISADKEN.SIKLTS   49

51  GLSVAASCLVVLENLLVLAAITSHMRSQRWVYYCLVNITMSDLLTGAAYL  100
     .:  :  :|:::|||::|| .|  . .: :| :|| :.|:..:||||.|.||
 50  VVFILICCFIILENIFVLLTIWKTKKFHRPMYYFIGNLALSDLLAGVAYT   99

101  ANVLLSGARTFRLAPAQWFLRKGLLFTALAASTFSLLFTAGLRFATMVRP  150
     ||:||||| |::|.||||||||.| :|.||.||.|||| .|  |: ||::
100  ANLLLSGATTYKLTPAQWFLREGSMFVALSASVFSLLAIAIERYITMLKM  149

151  VAESGATKTSRVYGFIGLCWLLAALLGMLPLLGWNCLCAFDRCSSLLPLY  200
     ..|. .. |:: :|: |||::. :|| ||::|||||::|:..||.:||||
150  KLHNGS.NNFRLFLLISACWVISLILGGLPIMGWNCISALSSCSTVLPLY  198

201  SKRYILFCLVIFAGVLATIMGLYGAIFRLVQASGQKAPRPAARRKARR..  248
     |:||||| .:|. :| .|: ||. |:.||...:: . . . .||.|
199  HKHYILFCTTVFTLLLLSIVILYCRIYSLVRTSRRLTFRKNISKASRSS   248

249  ....LLKTVLMILLAFLVCWGPLFGLLLADVFGSNLWAQEYLRGMDWILA  294
         |||||:::| .|:.||:||| ||| || |:.:.. :.|   :::|.
249  ENVALLKTVIIVLSVFIACWAPLFILLLLDV.GCKVKTCDILFRAEYFLV  297

295  LAVLNSAVNPIIYSFRSREVCRAVLSFLCCGCLRLGMRGPGDCLARAVEA  344
     ||||||:.|||||.|: .:|: ||.:.:::|.  .|  :.:: : |:: |
298  LAVLNSGTNPIIYTLTNKEMRRAFIRIMSCCKCPSG..DSAGKFKRPIIA  345

345  ...HSGASTTDSSLRPRDSFRGSRSLSFRMREPLSSIS    379
        | ....:||  ..:|.  |... .:.  .: :.| |
346  GMEFSRSKSDNSSHPQKDE..GDNPETIMSSGNVNSSS   381
```

FIG.4

SEQUENCE LISTING

<160> NUMBER OF SEQ ID NOS: 18

<210> SEQ ID NO 1
<211> LENGTH: 2247
<212> TYPE: DNA
<213> ORGANISM: genomic
<220> FEATURE:
<221> NAME/KEY: CDS
<222> LOCATION: (226)..(1251)

<400> SEQUENCE: 1

```
gcacgaggaa cagaacactt tctcatgtcc agggtcagat tacaagagca ctcaagactt      60
tactgacgaa aactcaggaa atcctctatc acaaagaggt ttggcaacta aactaagaca     120
ttaaaaggaa aataccagat gccactctgc aggctgcaat aactactact tactggatac     180
attcaaaccc tccagaatca acagttatca ggtaaccaac aagaa atg caa gcc gtc     237
                                                  Met Gln Ala Val
                                                   1 gac aat ctc acc tct gcg cct ggg aac acc agt ctg tgc acc aga gac      285
```

```
Asp Asn Leu Thr Ser Ala Pro Gly Asn Thr Ser Leu Cys Thr Arg Asp
 5                  10                  15                  20 tac aaa atc acc cag gtc ctc ttc cca ctg ctc tac act gtc ctg ttt        333
Tyr Lys Ile Thr Gln Val Leu Phe Pro Leu Leu Tyr Thr Val Leu Phe
             25                  30                  35 ttt gtt gga ctt atc aca aat ggc ctg gcg atg agg att ttc ttt caa        381
Phe Val Gly Leu Ile Thr Asn Gly Leu Ala Met Arg Ile Phe Phe Gln
                 40                  45                  50 atc cgg agt aaa tca aac ttt att att ttt ctt aag aac aca gtc att        429
Ile Arg Ser Lys Ser Asn Phe Ile Ile Phe Leu Lys Asn Thr Val Ile
             55                  60                  65 tct gat ctt ctc atg att ctg act ttt cca ttc aaa att ctt agt gat        477
Ser Asp Leu Leu Met Ile Leu Thr Phe Pro Phe Lys Ile Leu Ser Asp
 70                  75                  80 gcc aaa ctg gga aca gga cca ctg aga act ttt gtg tgt caa gtt acc        525
Ala Lys Leu Gly Thr Gly Pro Leu Arg Thr Phe Val Cys Gln Val Thr
 85                  90                  95                 100 tcc gtc ata ttt tat ttc aca atg tat atc agt att tca ttc ctg gga        573
Ser Val Ile Phe Tyr Phe Thr Met Tyr Ile Ser Ile Ser Phe Leu Gly
                105                 110                 115 ctg ata act atc gat cgc tac cag aag acc acc agg cca ttt aaa aca        621
Leu Ile Thr Ile Asp Arg Tyr Gln Lys Thr Thr Arg Pro Phe Lys Thr
            120                 125                 130 tcc aac ccc aaa aat ctc ttg ggg gct aag att ctc tct gtt gtc atc        669
Ser Asn Pro Lys Asn Leu Leu Gly Ala Lys Ile Leu Ser Val Val Ile
            135                 140                 145 tgg gca ttc atg ttc tta ctc tct ttg cct aac atg att ctg acc aac        717
Trp Ala Phe Met Phe Leu Leu Ser Leu Pro Asn Met Ile Leu Thr Asn
150                 155                 160 agg cag ccg aga gac aag aat gtg aag aaa tgc tct ttc ctt aaa tca        765
Arg Gln Pro Arg Asp Lys Asn Val Lys Lys Cys Ser Phe Leu Lys Ser
165                 170                 175                 180 gag ttc ggt cta gtc tgg cat gaa ata gta aat tac atc tgt caa gtc        813
Glu Phe Gly Leu Val Trp His Glu Ile Val Asn Tyr Ile Cys Gln Val
                185                 190                 195 att ttc tgg att aat ttc tta att gtt att gta tgt tat aca ctc att        861
Ile Phe Trp Ile Asn Phe Leu Ile Val Ile Val Cys Tyr Thr Leu Ile
            200                 205                 210 aca aaa gaa ctg tac cgg tca tac gta aga acg agg ggt gta ggt aaa        909
Thr Lys Glu Leu Tyr Arg Ser Tyr Val Arg Thr Arg Gly Val Gly Lys
            215                 220                 225 gtc ccc agg aaa aag gtg aac gtc aaa gtt ttc att atc att gct gta        957
Val Pro Arg Lys Lys Val Asn Val Lys Val Phe Ile Ile Ile Ala Val
230                 235                 240 ttc ttt att tgt ttt gtt cct ttc cat ttt gcc cga att cct tac acc       1005
Phe Phe Ile Cys Phe Val Pro Phe His Phe Ala Arg Ile Pro Tyr Thr
245                 250                 255                 260 ctg agc caa acc cgg gat gtc ttt gac tgc act gct gaa aat act ctg       1053
Leu Ser Gln Thr Arg Asp Val Phe Asp Cys Thr Ala Glu Asn Thr Leu
                265                 270                 275 ttc tat gtg aaa gag agc act ctg tgg tta act tcc tta aat gca tgc       1101
Phe Tyr Val Lys Glu Ser Thr Leu Trp Leu Thr Ser Leu Asn Ala Cys
            280                 285                 290 ctg gat ccg ttc atc tat ttt ttc ctt tgc aag tcc ttc aga aat tcc       1149
Leu Asp Pro Phe Ile Tyr Phe Phe Leu Cys Lys Ser Phe Arg Asn Ser
            295                 300                 305 ttg ata agt atg ctg aag tgc ccc aat tct gca aca tct ctg tcc cag       1197
Leu Ile Ser Met Leu Lys Cys Pro Asn Ser Ala Thr Ser Leu Ser Gln
310                 315                 320
```

-continued

```
gac aat agg aaa aaa gaa cag gat ggt ggt gac cca aat gaa gag act    1245
Asp Asn Arg Lys Lys Glu Gln Asp Gly Gly Asp Pro Asn Glu Glu Thr
325                 330                 335                 340 cca atg taaacaaatt aactaaggaa atatttcaat ctctttgtgt tcagaactcg     1301
Pro Met ttaaagcaaa gcgctaagta aaatattaa ctgacgaaga agcaactaag ttaataataa   1361
tgactctaaa gaaacagaag attacaaaag caattttcat ttacctttcc agtatgaaaa  1421
gctatcttaa aatatagaaa actaatctaa actgtagctg tattagcagc aaaacaaacg  1481
acatccaatt gtcatgctgc atgcaaaact acacagaatt catgttttgg cagagttttg  1541
gcaaaatgag taatcatata atatttactg taattttaa aatacattat cgttcacaat   1601 tttattttt cataatcaac taaggaagaa cgatcaattg gatataatct tcttaccaaa   1661
aatgatagtt aaaatgtata tatatcctag tcccctaacc aaatcctgac ctattgggat  1721
acttataaaa atttaagtaa gtgggataca caaagaataa taactattaa cttttcatta  1781
ttagccaaaa acctaaggga tttaaactaa ttgaaactgt atttgattgg acttaatttt  1841
ttatgtttat ttagaagata aagatttaag aagacctttta caataaagag aagaaatatc 1901 gaagtcatta aaataaggag acttactttt atgacattct aatactaaaa aatatagaaa  1961
tatttcctta attctagaga aactagtttt actaattttt tacaacttca ataataccat  2021
cactgacact tacctttatt aattagcttc tagaaaatag ctgctaatta ggttaatgaa  2081 catttttacct tagtgaaaaa aaattaatta aatatgatta caaagttgca cagcataact  2141
actgagagga aagtgattga tctgtttgta attacttgtt tgtattggtg tgtataaaat  2201
acaaatttac attaaactct aaatcattaa aaaaaaaaa aaaaaa                 2247
```

<210> SEQ ID NO 2
<211> LENGTH: 342
<212> TYPE: PRT
<213> ORGANISM: genomic

<400> SEQUENCE: 2

```
Met Gln Ala Val Asp Asn Leu Thr Ser Ala Pro Gly Asn Thr Ser Leu
 1               5                  10                  15

Cys Thr Arg Asp Tyr Lys Ile Thr Gln Val Leu Phe Pro Leu Leu Tyr
            20                  25                  30

Thr Val Leu Phe Phe Val Gly Leu Ile Thr Asn Gly Leu Ala Met Arg
        35                  40                  45

Ile Phe Phe Gln Ile Arg Ser Lys Ser Asn Phe Ile Ile Phe Leu Lys
    50                  55                  60

Asn Thr Val Ile Ser Asp Leu Leu Met Ile Leu Thr Phe Pro Phe Lys
65                  70                  75                  80

Ile Leu Ser Asp Ala Lys Leu Gly Thr Gly Pro Leu Arg Thr Phe Val
                85                  90                  95

Cys Gln Val Thr Ser Val Ile Phe Tyr Phe Thr Met Tyr Ile Ser Ile
            100                 105                 110

Ser Phe Leu Gly Leu Ile Thr Ile Asp Arg Tyr Gln Lys Thr Thr Arg
        115                 120                 125

Pro Phe Lys Thr Ser Asn Pro Lys Asn Leu Leu Gly Ala Lys Ile Leu
    130                 135                 140

Ser Val Val Ile Trp Ala Phe Met Phe Leu Leu Ser Leu Pro Asn Met
145                 150                 155                 160

Ile Leu Thr Asn Arg Gln Pro Arg Asp Lys Asn Val Lys Lys Cys Ser
```

```
                165                 170                 175
Phe Leu Lys Ser Glu Phe Gly Leu Val Trp His Glu Ile Val Asn Tyr
            180                 185                 190

Ile Cys Gln Val Ile Phe Trp Ile Asn Phe Leu Ile Val Ile Val Cys
        195                 200                 205

Tyr Thr Leu Ile Thr Lys Glu Leu Tyr Arg Ser Tyr Val Arg Thr Arg
    210                 215                 220

Gly Val Gly Lys Val Pro Arg Lys Val Asn Val Lys Val Phe Ile
225                 230                 235                 240

Ile Ile Ala Val Phe Phe Ile Cys Phe Val Pro His Phe Ala Arg
                245                 250                 255

Ile Pro Tyr Thr Leu Ser Gln Thr Arg Asp Val Phe Asp Cys Thr Ala
            260                 265                 270

Glu Asn Thr Leu Phe Tyr Val Lys Glu Ser Thr Leu Trp Leu Thr Ser
        275                 280                 285

Leu Asn Ala Cys Leu Asp Pro Phe Ile Tyr Phe Phe Leu Cys Lys Ser
    290                 295                 300

Phe Arg Asn Ser Leu Ile Ser Met Leu Lys Cys Pro Asn Ser Ala Thr
305                 310                 315                 320

Ser Leu Ser Gln Asp Asn Arg Lys Lys Glu Gln Asp Gly Gly Asp Pro
                325                 330                 335

Asn Glu Glu Thr Pro Met
            340

<210> SEQ ID NO 3
<211> LENGTH: 1637
<212> TYPE: DNA
<213> ORGANISM: genomic
<220> FEATURE:
<221> NAME/KEY: CDS
<222> LOCATION: (50)..(1201)

<400> SEQUENCE: 3
ggcacgagcc caccctgcgt cgggcctcag tcagccccg ggggaggcc atg aac gcc      58
                                                   Met Asn Ala
                                                     1 acg ggg acc ccg gtg gcc ccc gag tcc tgc caa cag ctg gcg gcc ggc     106
Thr Gly Thr Pro Val Ala Pro Glu Ser Cys Gln Gln Leu Ala Ala Gly
      5                  10                  15 ggg cac agc cgg ctc att gtt ctg cac tac aac cac tcg ggc cgg ctg     154
Gly His Ser Arg Leu Ile Val Leu His Tyr Asn His Ser Gly Arg Leu
 20                  25                  30                  35 gcc ggg cgc ggg ggg ccg gag gat ggc ggc ctg ggg gcc ctg cgg ggg     202
Ala Gly Arg Gly Gly Pro Glu Asp Gly Gly Leu Gly Ala Leu Arg Gly
                 40                  45                  50 ctg tcg gtg gcc gcc agc tgc ctg gtg gtg ctg gag aac ttg ctg gtg     250
Leu Ser Val Ala Ala Ser Cys Leu Val Val Leu Glu Asn Leu Leu Val
             55                  60                  65 ctg gcg gcc atc acc agc cac atg cgg tcg caa cgc tgg gtc tac tat     298
Leu Ala Ala Ile Thr Ser His Met Arg Ser Gln Arg Trp Val Tyr Tyr
         70                  75                  80 tgc ctg gtg aac att acg atg agt gac ctg ctc acg ggc gcg gcc tac     346
Cys Leu Val Asn Ile Thr Met Ser Asp Leu Leu Thr Gly Ala Ala Tyr
     85                  90                  95 ctg gcc aac gtg ctg ctg tcg ggg gcc cgc acc ttc cgt ctg gcg ccc     394
Leu Ala Asn Val Leu Leu Ser Gly Ala Arg Thr Phe Arg Leu Ala Pro
100                 105                 110                 115 gcc cag tgg ttc cta cgg aag ggc ctg ctc ttc acc gcc ctg gcc gcc     442
```

```
Ala Gln Trp Phe Leu Arg Lys Gly Leu Leu Phe Thr Ala Leu Ala Ala
            120                 125                 130 tcc acc ttc agc ctg ctc ttc act gca ggg ttg cgc ttt gcc acc atg           490
Ser Thr Phe Ser Leu Leu Phe Thr Ala Gly Leu Arg Phe Ala Thr Met
        135                 140                 145 gtg cgg ccg gtg gcc gag agc ggg gcc acc aag acc agc cgc gtc tac           538
Val Arg Pro Val Ala Glu Ser Gly Ala Thr Lys Thr Ser Arg Val Tyr
    150                 155                 160 ggc ttc atc ggc ctc tgc tgg ctg ctg gcc gcg ctg ctg ggg atg ctg           586
Gly Phe Ile Gly Leu Cys Trp Leu Leu Ala Ala Leu Leu Gly Met Leu
165                 170                 175 cct ttg ctg ggc tgg aac tgc ctg tgc gcc ttt gac cgc tgc tcc agc           634
Pro Leu Leu Gly Trp Asn Cys Leu Cys Ala Phe Asp Arg Cys Ser Ser
180                 185                 190                 195 ctt ctg ccc ctc tac tcc aag cgc tac atc ctc ttc tgc ctg gtg atc           682
Leu Leu Pro Leu Tyr Ser Lys Arg Tyr Ile Leu Phe Cys Leu Val Ile
                200                 205                 210 ttc gcc ggc gtc ctg gcc acc atc atg ggc ctc tat ggg gcc atc ttc           730
Phe Ala Gly Val Leu Ala Thr Ile Met Gly Leu Tyr Gly Ala Ile Phe
            215                 220                 225 cgc ctg gtg cag gcc agc ggg cag aag gcc cca cgc cca gcg gcc cgc           778
Arg Leu Val Gln Ala Ser Gly Gln Lys Ala Pro Arg Pro Ala Ala Arg
        230                 235                 240 cgc aag gcc cgc cgc ctg ctg aag acg gtg ctg atg atc ctg ctg gcc           826
Arg Lys Ala Arg Arg Leu Leu Lys Thr Val Leu Met Ile Leu Leu Ala
    245                 250                 255 ttc ttg gtg tgc tgg gga cca ctc ttc ggg ctg ctg ctg gcc gac gtc           874
Phe Leu Val Cys Trp Gly Pro Leu Phe Gly Leu Leu Leu Ala Asp Val
260                 265                 270                 275 ttt ggc tcc aac ctc tgg gcc cag gag tac ctg cgg ggc atg gac tgg           922
Phe Gly Ser Asn Leu Trp Ala Gln Glu Tyr Leu Arg Gly Met Asp Trp
                280                 285                 290 atc ctg gcc ctg gcc gtc ctc aac tcg gcg gtc aac ccc atc atc tac           970
Ile Leu Ala Leu Ala Val Leu Asn Ser Ala Val Asn Pro Ile Ile Tyr
            295                 300                 305 tcc ttc cgc agc agg gag gtg tgc aga gcc gtg ctc agc ttc ctc tgc          1018
Ser Phe Arg Ser Arg Glu Val Cys Arg Ala Val Leu Ser Phe Leu Cys
        310                 315                 320 tgc ggg tgt ctc cgg ctg ggc atg cga ggg ccc ggg gac tgc ctg gcc          1066
Cys Gly Cys Leu Arg Leu Gly Met Arg Gly Pro Gly Asp Cys Leu Ala
    325                 330                 335 cgg gcc gtc gag gct cac tcc gga gct tcc acc acc gac agc tct ctg          1114
Arg Ala Val Glu Ala His Ser Gly Ala Ser Thr Thr Asp Ser Ser Leu
340                 345                 350                 355 agg cca agg gac agc ttt cgc ggc tcc cgc tcg ctc agc ttt cgg atg          1162
Arg Pro Arg Asp Ser Phe Arg Gly Ser Arg Ser Leu Ser Phe Arg Met
                360                 365                 370 cgg gag ccc ctg tcc agc atc tcc agc gtg cgg agc atc tgaagttgca          1211
Arg Glu Pro Leu Ser Ser Ile Ser Ser Val Arg Ser Ile
            375                 380 gtcttgcgtg tggatggtgc aaccaccggg tgcgtgccag gcaggccctc ctggggtaca       1271
ggaagctgtg tgcacgcaac ctcgccctgt atggggagca gggaacggga caggcccca         1331 tggacttgcc cggtggcctc tcggggcttc tgacgccata tggacttgcc cattgcctat       1391
ggctcaccct ggacaaggag gcaaccaccc cacctccccg taggagcaga gagcaccctg       1451 gtgtggggc gagtgggttc cccacaaccc cgcttcgtgt tgattctggg gaagtcccgg        1511
cccctctctg ggcctcagta gggctcccag gctgcaaggg gtggactgtg ggatgcatgc       1571
```

```
cctggcaaca ttgaagttcg atcatggtaa aaaaaaaaaa aaaaaaaaaa aaaaaaaaaa    1631
aaaaaa                                                              1637

<210> SEQ ID NO 4
<211> LENGTH: 384
<212> TYPE: PRT
<213> ORGANISM: genomic

<400> SEQUENCE: 4
```

| Met | Asn | Ala | Thr | Gly | Thr | Pro | Val | Ala | Pro | Glu | Ser | Cys | Gln | Gln | Leu |
|-----|-----|-----|-----|-----|-----|-----|-----|-----|-----|-----|-----|-----|-----|-----|-----|
| 1 | | | | 5 | | | | | 10 | | | | | 15 | |

| Ala | Ala | Gly | Gly | His | Ser | Arg | Leu | Ile | Val | Leu | His | Tyr | Asn | His | Ser |
| | | | 20 | | | | | 25 | | | | | 30 | | |

| Gly | Arg | Leu | Ala | Gly | Arg | Gly | Pro | Glu | Asp | Gly | Leu | Gly | Ala |
| | | 35 | | | | | 40 | | | | | 45 | |

| Leu | Arg | Gly | Leu | Ser | Val | Ala | Ala | Ser | Cys | Leu | Val | Val | Leu | Glu | Asn |
| | 50 | | | | | 55 | | | | | 60 | | | | |

| Leu | Leu | Val | Leu | Ala | Ala | Ile | Thr | Ser | His | Met | Arg | Ser | Gln | Arg | Trp |
| 65 | | | | | 70 | | | | | 75 | | | | | 80 |

| Val | Tyr | Tyr | Cys | Leu | Val | Asn | Ile | Thr | Met | Ser | Asp | Leu | Leu | Thr | Gly |
| | | | | 85 | | | | | 90 | | | | | 95 | |

| Ala | Ala | Tyr | Leu | Ala | Asn | Val | Leu | Leu | Ser | Gly | Ala | Arg | Thr | Phe | Arg |
| | | | 100 | | | | | 105 | | | | | 110 | | |

| Leu | Ala | Pro | Ala | Gln | Trp | Phe | Leu | Arg | Lys | Gly | Leu | Leu | Phe | Thr | Ala |
| | | 115 | | | | | 120 | | | | | 125 | | | |

| Leu | Ala | Ala | Ser | Thr | Phe | Ser | Leu | Leu | Phe | Thr | Ala | Gly | Leu | Arg | Phe |
| | 130 | | | | | 135 | | | | | 140 | | | | |

| Ala | Thr | Met | Val | Arg | Pro | Val | Ala | Glu | Ser | Gly | Ala | Thr | Lys | Thr | Ser |
| 145 | | | | | 150 | | | | | 155 | | | | | 160 |

| Arg | Val | Tyr | Gly | Phe | Ile | Gly | Leu | Cys | Trp | Leu | Leu | Ala | Ala | Leu | Leu |
| | | | | 165 | | | | | 170 | | | | | 175 | |

| Gly | Met | Leu | Pro | Leu | Leu | Gly | Trp | Asn | Cys | Leu | Cys | Ala | Phe | Asp | Arg |
| | | | 180 | | | | | 185 | | | | | 190 | | |

| Cys | Ser | Ser | Leu | Leu | Pro | Leu | Tyr | Ser | Lys | Arg | Tyr | Ile | Leu | Phe | Cys |
| | | 195 | | | | | 200 | | | | | 205 | | | |

| Leu | Val | Ile | Phe | Ala | Gly | Val | Leu | Ala | Thr | Ile | Met | Gly | Leu | Tyr | Gly |
| | 210 | | | | | 215 | | | | | 220 | | | | |

| Ala | Ile | Phe | Arg | Leu | Val | Gln | Ala | Ser | Gly | Gln | Lys | Ala | Pro | Arg | Pro |
| 225 | | | | | 230 | | | | | 235 | | | | | 240 |

| Ala | Ala | Arg | Arg | Lys | Ala | Arg | Arg | Leu | Leu | Lys | Thr | Val | Leu | Met | Ile |
| | | | | 245 | | | | | 250 | | | | | 255 | |

| Leu | Leu | Ala | Phe | Leu | Val | Cys | Trp | Gly | Pro | Leu | Phe | Gly | Leu | Leu | Leu |
| | | | 260 | | | | | 265 | | | | | 270 | | |

| Ala | Asp | Val | Phe | Gly | Ser | Asn | Leu | Trp | Ala | Gln | Glu | Tyr | Leu | Arg | Gly |
| | | 275 | | | | | 280 | | | | | 285 | | | |

| Met | Asp | Trp | Ile | Leu | Ala | Leu | Ala | Val | Leu | Asn | Ser | Ala | Val | Asn | Pro |
| | 290 | | | | | 295 | | | | | 300 | | | | |

| Ile | Ile | Tyr | Ser | Phe | Arg | Ser | Arg | Glu | Val | Cys | Arg | Ala | Val | Leu | Ser |
| 305 | | | | | 310 | | | | | 315 | | | | | 320 |

| Phe | Leu | Cys | Cys | Gly | Cys | Leu | Arg | Leu | Gly | Met | Arg | Gly | Pro | Gly | Asp |
| | | | | 325 | | | | | 330 | | | | | 335 | |

| Cys | Leu | Ala | Arg | Ala | Val | Glu | Ala | His | Ser | Gly | Ala | Ser | Thr | Thr | Asp |
| | | | 340 | | | | | 345 | | | | | 350 | | |

| Ser | Ser | Leu | Arg | Pro | Arg | Asp | Ser | Phe | Arg | Gly | Ser | Arg | Ser | Leu | Ser |

```
                    355                 360                 365
                Phe Arg Met Arg Glu Pro Leu Ser Ser Ile Ser Ser Val Arg Ser Ile
                    370                 375                 380

<210> SEQ ID NO 5
<211> LENGTH: 28
<212> TYPE: DNA
<213> ORGANISM: genomic

<400> SEQUENCE: 5
ccgaggatcc atgcaagccg tcgacaat                                          28

<210> SEQ ID NO 6
<211> LENGTH: 28
<212> TYPE: DNA
<213> ORGANISM: genomic

<400> SEQUENCE: 6
ccgaggatcc ttacattgga gtctcttc                                          28

<210> SEQ ID NO 7
<211> LENGTH: 34
<212> TYPE: DNA
<213> ORGANISM: genomic

<400> SEQUENCE: 7
ccgaggatcc gccatcatgc aagccgtcga caat                                   34

<210> SEQ ID NO 8
<211> LENGTH: 28
<212> TYPE: DNA
<213> ORGANISM: genomic

<400> SEQUENCE: 8
ccgaggatcc ttacattgga gtctcttc                                          28

<210> SEQ ID NO 9
<211> LENGTH: 34
<212> TYPE: DNA
<213> ORGANISM: genomic

<400> SEQUENCE: 9
ccgaggatcc gccatcatgc aagccgtcga caat                                   34

<210> SEQ ID NO 10
<211> LENGTH: 55
<212> TYPE: DNA
<213> ORGANISM: genomic

<400> SEQUENCE: 10
ccgatctaga ttaatcccat acgacgtccc agactacgct cattggagtc tcttc            55

<210> SEQ ID NO 11
<211> LENGTH: 28
<212> TYPE: DNA
<213> ORGANISM: genomic

<400> SEQUENCE: 11
ccgaggatcc atgaacgcca cggggacc                                          28

<210> SEQ ID NO 12
<211> LENGTH: 28
<212> TYPE: DNA
```

```
<213> ORGANISM: genomic

<400> SEQUENCE: 12
ccgaggatcc tcagatgctc cgcacgct                              28

<210> SEQ ID NO 13
<211> LENGTH: 34
<212> TYPE: DNA
<213> ORGANISM: genomic

<400> SEQUENCE: 13
gcgaggatcc gccatcatga acgccacggg gacc                       34

<210> SEQ ID NO 14
<211> LENGTH: 28
<212> TYPE: DNA
<213> ORGANISM: genomic

<400> SEQUENCE: 14
ccgaggatcc tcagatgctc cgcacgct                              28

<210> SEQ ID NO 15
<211> LENGTH: 34
<212> TYPE: DNA
<213> ORGANISM: genomic

<400> SEQUENCE: 15
ccgaggatcc gccatcatga acgccacggg gacc                       34

<210> SEQ ID NO 16
<211> LENGTH: 55
<212> TYPE: DNA
<213> ORGANISM: genomic

<400> SEQUENCE: 16
ccgatctaga tcaatcccat acgacgtccc agactacgct gatgctccgc acgct    55

<210> SEQ ID NO 17
<211> LENGTH: 348
<212> TYPE: PRT
<213> ORGANISM: genomic

<400> SEQUENCE: 17
```

Ile Gln Met Ala Asn Asn Phe Thr Pro Pro Ser Ala Thr Pro Gln Asn
 1               5                  10                  15

Asp Cys Asp Leu Tyr Ala His His Ser Thr Ala Arg Ile Val Met Pro
                20                  25                  30

Leu His Tyr Ser Leu Val Phe Ile Ile Gly Leu Val Gly Asn Leu Leu
            35                  40                  45

Ala Leu Val Val Ile Val Gln Asn Arg Lys Lys Ile Asn Ser Thr Thr
        50                  55                  60

Leu Tyr Ser Thr Asn Leu Val Ile Ser Asp Ile Leu Phe Thr Thr Ala
    65                  70                  75                  80

Leu Pro Thr Arg Ile Ala Tyr Tyr Ala Met Gly Phe Asp Trp Arg Ile
                85                  90                  95

Gly Asp Ala Leu Cys Arg Ile Thr Ala Leu Val Phe Tyr Ile Asn Thr
                100                 105                 110

Tyr Ala Gly Val Asn Phe Met Thr Cys Leu Ser Ile Asp Arg Phe Ile
            115                 120                 125

Ala Val Val His Pro Leu Arg Tyr Asn Lys Ile Lys Arg Ile Glu His

-continued

```
                130                 135                 140
Ala Lys Gly Val Cys Ile Phe Val Trp Ile Leu Val Phe Ala Gln Thr
145                 150                 155                 160

Leu Pro Leu Leu Ile Asn Pro Met Ser Lys Gln Glu Ala Glu Arg Ile
                165                 170                 175

Thr Cys Met Glu Tyr Pro Asn Phe Glu Glu Thr Lys Ser Leu Pro Trp
            180                 185                 190

Ile Leu Leu Gly Ala Cys Phe Ile Gly Tyr Val Leu Pro Leu Ile Ile
            195                 200                 205

Ile Lys Ile Cys Tyr Ser Gln Ile Cys Cys Lys Leu Phe Arg Thr Ala
            210                 215                 220

Lys Gln Asn Pro Leu Thr Glu Lys Ser Gly Val Asn Lys Lys Ala Leu
225                 230                 235                 240

Asn Thr Ile Ile Leu Ile Val Val Phe Val Leu Cys Phe Thr Pro
                245                 250                 255

Tyr His Val Ala Ile Ile Gln His Met Ile Lys Lys Leu Arg Phe Ser
            260                 265                 270

Asn Phe Leu Glu Cys Ser Gln Arg His Ser Phe Gln Ile Ser Leu His
            275                 280                 285

Phe Thr Val Cys Leu Met Asn Phe Asn Cys Cys Met Asp Pro Phe Ile
            290                 295                 300

Tyr Phe Phe Ala Cys Lys Gly Tyr Lys Arg Lys Val Met Arg Met Leu
305                 310                 315                 320

Lys Arg Gln Val Ser Val Ser Ile Ser Ser Ala Val Lys Ser Ala Pro
                325                 330                 335

Glu Glu Asn Ser Arg Glu Met Thr Glu Thr Gln Met
                340                 345

<210> SEQ ID NO 18
<211> LENGTH: 381
<212> TYPE: PRT
<213> ORGANISM: genomic

<400> SEQUENCE: 18

Met Gly Pro Thr Ser Val Pro Leu Val Lys Ala His Arg Ser Ser Val
1               5                   10                  15

Ser Asp Tyr Val Asn Tyr Asp Ile Ile Val Arg His Tyr Asn Tyr Thr
                20                  25                  30

Gly Lys Leu Asn Ile Ser Ala Asp Lys Glu Asn Ser Ile Lys Leu Thr
            35                  40                  45

Ser Val Val Phe Ile Leu Ile Cys Cys Phe Ile Ile Leu Glu Asn Ile
        50                  55                  60

Phe Val Leu Leu Thr Ile Trp Lys Thr Lys Lys Phe His Arg Pro Met
65                  70                  75                  80

Tyr Tyr Phe Ile Gly Asn Leu Ala Leu Ser Asp Leu Leu Ala Gly Val
                85                  90                  95

Ala Tyr Thr Ala Asn Leu Leu Leu Ser Gly Ala Thr Thr Tyr Lys Leu
                100                 105                 110

Thr Pro Ala Gln Trp Phe Leu Arg Glu Gly Ser Met Phe Val Ala Leu
            115                 120                 125

Ser Ala Ser Val Phe Ser Leu Leu Ala Ile Ala Ile Glu Arg Tyr Ile
        130                 135                 140

Thr Met Leu Lys Met Lys Leu His Asn Gly Ser Asn Asn Phe Arg Leu
145                 150                 155                 160
```

-continued

```
Phe Leu Leu Ile Ser Ala Cys Trp Val Ile Ser Leu Ile Leu Gly Gly
             165             170             175

Leu Pro Ile Met Gly Trp Asn Cys Ile Ser Ala Leu Ser Ser Cys Ser
             180             185             190

Thr Val Leu Pro Leu Tyr His Lys His Tyr Ile Leu Phe Cys Thr Thr
        195             200             205

Val Phe Thr Leu Leu Leu Ser Ile Val Ile Leu Tyr Cys Arg Ile
    210             215             220

Tyr Ser Leu Val Arg Thr Arg Ser Arg Arg Leu Thr Phe Arg Lys Asn
225             230             235             240

Ile Ser Lys Ala Ser Arg Ser Ser Glu Asn Val Ala Leu Leu Lys Thr
             245             250             255

Val Ile Ile Val Leu Ser Val Phe Ile Ala Cys Trp Ala Pro Leu Phe
             260             265             270

Ile Leu Leu Leu Leu Asp Val Gly Cys Lys Val Lys Thr Cys Asp Ile
             275             280             285

Leu Phe Arg Ala Glu Tyr Phe Leu Val Leu Ala Val Leu Asn Ser Gly
        290             295             300

Thr Asn Pro Ile Ile Tyr Thr Leu Thr Asn Lys Glu Met Arg Arg Ala
305             310             315             320

Phe Ile Arg Ile Met Ser Cys Cys Lys Cys Pro Ser Gly Asp Ser Ala
             325             330             335

Gly Lys Phe Lys Arg Pro Ile Ile Ala Gly Met Glu Phe Ser Arg Ser
             340             345             350

Lys Ser Asp Asn Ser Ser His Pro Gln Lys Asp Glu Gly Asp Asn Pro
             355             360             365

Glu Thr Ile Met Ser Ser Gly Asn Val Asn Ser Ser Ser
        370             375             380
```

HUMAN G-PROTEIN COUPLED RECEPTORS

BACKGROUND OF THE INVENTION

1. Field of the Invention

This invention relates to newly identified polynucleotides, polypeptides encoded by such polynucleotides, the use of such polynucleotides and polypeptides, as well as the production of such polynucleotides and polypeptides. More particularly, the polypeptides of the present invention are a human EBV-induced G-protein coupled receptor (EBI-2) and a human EDG-1-like G-protein coupled receptor, sometimes hereinafter referred to singularly as "GBR" or "GPCR" and collectively as "GBRs." The invention also relates to inhibiting the action of such polypeptides.

2. Related Art

At least nine genes have been identified that are apparently activated in response to an Epstein-Barr Virus (EBV) infection. One of two novel genes also identified in such studies of EBV infections was a novel GPCR-like cDNA molecule designated EBV-induced G-protein coupled receptor (EBI)-1.

Additionally, previously identified was an endothelium-differentiation gene (EDG) that was obtained from PMA-simulated human endothelial cells. Rat and sheep homologs of EDG-1 have been identified, which are also G-protein coupled receptors.

It is well established that many medically significant biological processes are mediated by proteins participating in signal transduction pathways that involve G-proteins and/or second messengers, e.g., cAMP (Lefkowitz, Nature, 351:353–354 (1991)). Herein these proteins are referred to as proteins participating in pathways with G-proteins or PPG proteins. Some examples of these proteins include the GPC receptors, such as those for adrenergic agents and dopamine (Kobilka, B. K., et al., PNAS, 84:46–50 (1987); Kobilka, B. K., et al., Science, 238:650–656 (1987); Bunzow, J. R., et al., Nature, 336:783–787 (1988)), G-proteins themselves, effector proteins, e.g., phospholipase C, adenyl cyclase, and phosphodiesterase, and actuator proteins, e.g., protein kinase A and protein kinase C (Simon, M. I., et al., Science, 252:802–8 (1991)).

For example, in one form of signal transduction, the effect of hormone binding is activation of an enzyme, adenylate cyclase, inside the cell. Enzyme activation by hormones is dependent on the presence of the nucleotide GTP, and GTP also influences hormone binding. A G-protein connects the hormone receptors to adenylate cyclase. G-protein was shown to exchange GTP for bound GDP when activated by hormone receptors. The GTP-carrying form then binds to an activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane α-helices connected by extracellular or cytoplasmic loops. A function G-protein is a trimer which consists of a variable alpha subunit coupled to a much more tightly-associated and constant beta and gamma subunits. A broad range of ligands (more than twenty) have been identified which function through GPCRs. In general, bind of an appropriate ligand to a GPCR leads to the activation of the receptor. G-protein coupled receptors include a wide range of biologically active receptors, such as hormone, viral, growth factor and neuroreceptors. Such an activated receptor initiates the regulatory cycle of the G-protein. This cycle consists of GTP exchange for GDP, dissociation of the alpha and beta/gamma subunits, activation of the second messenger pathway by a complex of GTP and th alpha subunit of the G-protein, and return to the resting state by GTP hydrolysis via the innate GTP-ase activity of the G-protein alpha subunit.A G-protein coupled receptors have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include calcitonin, adrenergic, endothelin, cAMP, adenosine, muscarinic, acetylcholine, serotonin, histamine, thrombin, kinin, follicle stimulating hormone, opsins and rhodopsins, odorant, cytomegalovirus receptors, etc.

Most GPRs have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. TM3 is also implicated in signal transduction.

Phosphorylation and lipidation (palmitylation or farnesylation) of cysteine residues can influence signal transduction of some GPRs. Most GPRs contain potential phosphorylation sites within the third cytoplasmic loop and/or the carboxy terminus. For several GPRs, such as the β-adrenoreceptor, phosphorylation by protein kinase A and/or specific receptor kinases mediates receptor desensitization.

The ligand binding sites of GPRs are believed to comprise a hydrophilic socket formed by several GPR transmembrane domains, which socket is surrounded by hydrophobic residues of the GPRs. The hydrophilic side of each GPR transmembrane helix is postulated to face inward and form the polar ligand binding site. TM3 has been implicated in several GPRs as having a ligand binding site, such as including the TM3 aspartate residue. Additionally, TM5 serines, a TM6 asparagine and TM6 or TM7 phenylalanines or tyrosines are also implicated in ligand binding.

GPRs can be intracellularly coupled by heterotrimeric G-proteins to various intracellular enzymes, ion channels and transporters (see, Johnson et al., Endoc., Rev., 10:317–331 (1989)). Different G-protein α-subunits preferentially stimulate particular effectors to modulate various biological functions in a cell. Phosphorylation of cytoplasmic residues of GPRs has been identified as an important mechanism for the regulation of G-protein coupling of some GPRs.

G-protein coupled receptors are found in numerous sites within a mammalian host, for example, dopamine is a critical neurotransmitter in the central nervous system and is a G-protein coupled receptor ligand.

In accordance with one aspect of the present invention, there are provided novel polypeptides, as well as antisense analogs thereof and biologically active and diagnostically or therapeutically useful fragments and derivatives thereof. The polypeptides of the present invention are of human origin.

SUMMARY OF THE INVENTION

In accordance with another aspect of the present invention, there are provided isolated nucleic acid molecules, including mRNAs, DNAs, cDNAS, genomic DNA as well as antisense analogs thereof and biologically active and diagnostically or therapeutically useful fragments thereof.

In accordance with a further aspect of the present invention, there is provided a process for producing such polypeptides by recombinant techniques which comprises culturing recombinant prokaryotic and/or eukaryotic host cells, containing a nucleic acid sequence encoding a polypeptide of the present invention, under conditions promoting expression of said protein and subsequent recovery of said protein.

In accordance with yet a further aspect of the present invention, there are provided antibodies against such polypeptides.

In accordance with another embodiment, there is provided a process for using one or more of the receptors according to the invention to screen for receptor antagonists and/or agonists and/or receptor ligands.

In accordance with still another embodiment of the present invention there is provided a process of using such agonists to activate the polypeptide of the present invention for the treatment of conditions related to the underexpression of the polypeptide of the present invention.

In accordance with another aspect of the present invention there is provided a process of using such antagonists for inhibiting the polypeptide of the present invention for treating conditions associated with overexpression of the polypeptide of the present invention.

In accordance with yet another aspect of the present invention there is provided non-naturally occurring synthetic, isolated and/or recombinant polypeptides which are fragments, consensus fragments and/or sequences having conservative amino acid substitutions, of at least one transmembrane domain, such that the polypeptides of the present invention may bind ligands, or which may also modulate, quantitatively or qualitatively, ligand binding to the polypeptide of the present invention.

In accordance with still another aspect of the present invention there are provided synthetic or recombinant polypeptides, conservative substitution derivatives thereof, antibodies, anti-idiotype antibodies, compositions and methods that can be useful as potential modulators of G-protein coupled receptor function, by binding to ligands or modulating ligand binding, due to their expected biological properties, which may be used in diagnostic, therapeutic and/or research applications.

In accordance with another object of the present invention, there is provided synthetic, isolated or recombinant polypeptides which are designed to inhibit or mimic various GPRs or fragments thereof, as receptor types and subtypes.

In accordance with yet another object of the present invention, there is provided a diagnostic assay for detecting a disease or susceptibility to a disease related to a mutation in a nucleic acid sequence encoding a polypeptide of the present invention.

These and other aspects of the present invention should be apparent to those skilled in the art from the teachings herein.

The following drawings are illustrative of embodiments of the invention and are not meant to limit the scope of the invention as encompassed by the claims.

BRIEF DESCRIPTION OF THE FIGURES

FIG. 1A, 1B and 1C show the cDNA sequence (SEQ ID NO:1) and the corresponding deduced amino acid sequence (SEQ ID NO:2) of the EBV-induced G-protein coupled receptor of the present invention. The polynucleotide sequence contains a 2249 nucleotide sequence which encodes a 342 amino acid ORF. In FIG. 1A to 1C, the standard one-letter abbreviation for amino acids is used to illustrate the deduced amino acid sequence. Sequencing was performed using a 373 Automated DNA sequencer (Applied Biosystems, Inc.). Sequencing accuracy is predicted to be greater than 97% accurate.

FIG. 2 is an amino acid sequence comparison between the EBV-induced (EBI-2) G-Protein Coupled Receptor (upper line, see SEQ ID NO:2) and the human EBI-1 G-Protein Coupled Receptor (lower line, SEQ ID NO:17). The standard one-letter abbreviations are used to represent the amino acid residues of the amino acid sequences illustrated. The EBI-2 polypeptide according to the invention shows approximately 25% identity and 49% similarity to the amino acid sequence of the EBI-1 gene over an approximately 350 amino acid stretch.

FIG. 3A and 3B show the cDNA sequence (SEQ ID NO:3) and the corresponding deduced amino acid sequence (SEQ ID NO:4) of the EDG-1-like G-protein coupled receptor of the present invention. The polynucleotide sequence contains a 1637 nucleotide sequence which encodes a 384 amino acid ORF. In FIG. 3A and 3B, the standard one-letter abbreviation for amino acids is used to illustrate the deduced amino acid sequence. Sequencing was performed using a 373 Automated DNA sequencer (Applied Biosystems, Inc.). Sequencing accuracy is predicted to be greater than 97% accurate.

FIG. 4 is an amino acid sequence comparison between the EDG-1-like G-Protein Coupled Receptor (upper line, see SEQ ID NO:4) and the human EDG-1 orphan G-Protein Coupled Receptor (lower line, SEQ ID NO:18). The standard one-letter abbreviations are used to represent the amino acid residues of the amino acid sequences illustrated. The EDG-1-like polypeptide according to the invention shows approximately 54% identity and 73% similarity to the amino acid sequence of the human EDG-1 orphan G-protein Coupled Receptor gene over two regions totaling approximately 120 amino acids.

DETAILED DESCRIPTION OF THE INVENTION

In accordance with an aspect of the present invention, there is provided an isolated nucleic acid (polynucleotide) which encode for the mature polypeptide having the deduced amino acid sequence of FIG. 1 (SEQ ID NO:2) or for the mature polypeptide encoded by the cDNA of the clone deposited with the American Type Culture Collection (ATCC), 10801 University Boulevard, Manassas, Va. 20110-2209as ATCC Deposit No. 209003 on Apr. 28, 1997.

A polynucleotide encoding a EBI-2 polypeptide of the present invention may be found in a cDNA library from umbilical vein endothelial cells, neutrophil leukocyte cells, and corpus colosum cells. The polynucleotide of this invention was discovered in a cDNA library derived from umbilical vein endothelial cells. As described above, it is structurally related to the G protein-coupled receptor family. It contains an open reading frame encoding a protein of 342 amino acid residues.

In accordance with an aspect of the present invention, there is provided an isolated nucleic acid (polynucleotide)

which encode for the mature polypeptide having the deduced amino acid sequence of FIG. 3 (SEQ ID NO:4) or for the mature polypeptide encoded by the cDNA of the clone deposited as ATCC Deposit No. 209004 on Apr. 28, 1997.

A polynucleotide encoding an EDG-1-like G-protein coupled receptor polypeptide of the present invention may be found in an activated neutrophil cDNA library, cyclohexamine-treated Raji cells, the RSR;11 bone marrow cell line, activated T-cells, tonsils, and CD34-positive cord blood cells. Northern blot analyses indicate that the EDG-1-like receptor gene is expressed primarily in leukocytes, but expression may also be observed in placenta, spleen, thymus, lung and pancreas tissue. The polynucleotide of this invention was discovered in a cDNA library derived from activated neutrophils. As described above, it is structurally related to the G protein-coupled receptor family. It contains an open reading frame encoding a protein of 384 amino acid residues.

As noted above a great deal of the importance attributed to GPCR molecules such as those of the presently claimed invention lies in the diversity of biological functions in which they participate. For example, it is thought that, upon release form the alpha subunit, the beta/gamma subunit may also play a functional role in the regulation of signal transduction by activating the arachidonic acid signal transduction pathway via the activation of phospholipase $A_2$. In addition, GPCR molecules and their associated G-proteins have been implicated in the coupling of visual pigments to CGMP phosphodiesterase, phosphatidyl inositol (PI) turnover, adenylyl cyclase signal channels and other integral membrane enzymes to transporter proteins. As a result, it is apparent that novel GPCR molecules may prove useful in a wide variety of pharmaceutical applications including research and development. For example, target based screens for small molecules and other such pharmacologically valuable factors may be based on activating a given GPCR. It has also been observed that short peptides may function by mimicking the GPCR (temed receptomimetics). Furthermore, monoclonal antibodies raised against such factors may prove useful as therapeutics in a number of capacities. Potential therapeutic and/or diagnositic applications for such a factor may include such diverse clinical presentations as heart disease, mental illness, cancer, atherosclerosis, restenosis, Alzheimer's Disease, Parkinson's Disease, and a number of others.

Accordingly, the polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature EBI-2 polypeptide may be identical to the coding sequence shown in FIG. 1 (SEQ ID NO:1) or that of the deposited clone or may be a different coding sequence which coding sequence, as a result of the redundancy or degeneracy of the genetic code, encodes the same mature polypeptide as the DNA of FIG. 1 (SEQ ID NO:1) or the deposited cDNA. Similarly, the coding sequence which encodes the mature EDG-1-like G-protein coupled receptor polypeptide may be identical to the coding sequence shown in FIG. 3 (SEQ ID NO:3) or that of the deposited clone or may be a different coding sequence which coding sequence, as a result of the redundancy or degeneracy of the genetic code, encodes the same mature polypeptide as the DNA of FIG. 3 (SEQ ID NO:3) or the deposited cDNA.

The polynucleotides which encode either (a) the mature EBI-2 polypeptide of FIG. 1 (SEQ ID NO:2) or the mature EBI-2 polypeptide encoded by the deposited cDNA, or (b) the mature EDG-1-like G-protein coupled receptor polypeptide of FIG. 3 (SEQ ID NO:4) or the mature EDG-1-like G-protein coupled receptor polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of (a) the polypeptide having the deduced amino acid sequence of FIG. 1 (SEQ ID NO:2) or the polypeptide encoded by the cDNA of the deposited clone, or (2) the polypeptide having the deduced amino acid sequence of FIG. 3 (SEQ ID NO:4) or the polypeptide encoded by the cDNA of the deposited clone, The variant of either of these two polynucleotides may be a naturally occurring allelic variant of the polynucleotide or a non-naturally occurring variant of the polynucleotide.

Thus, the present invention includes polynucleotides encoding the same mature polypeptide as shown in FIG. 1 (SEQ ID NO:2) or the same mature polypeptide encoded by the cDNA of the deposited clone as well as variants of such polynucleotides which variants encode for a fragment, derivative or analog of the polypeptide of FIG. 1 (SEQ ID NO:2) or the polypeptide encoded by the cDNA of the deposited clone. Such nucleotide variants include deletion variants, substitution variants and addition or insertion variants.

Likewise, the present invention includes polynucleotides encoding the same mature polypeptide as shown in FIG. 3 (SEQ ID NO:4) or the same mature polypeptide encoded by the cDNA of the deposited clone as well as variants of such polynucleotides which variants encode for a fragment, derivative or analog of the polypeptide of FIG. 3 (SEQ ID NO:4) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1) or of the coding sequence of the deposited clone. Also, as hereinabove indicated, the polynucleotide may have a coding sequence which is a naturally occurring allelic variant of the coding sequence shown in FIG. 3 (SEQ ID NO:3) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also code for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode a mature protein, or a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as hybridization probes for a cDNA or a genomic library to isolate the full length DNA and to isolate other DNAs which have a high sequence similarity to the gene or similar biological activity. Probes of this type preferably have at least 10, preferably at least 15, and even more preferably at least 30 bases and may contain, for example, at least 50 or more bases. In fact, probes of this type having at least up to 150 bases or greater may be preferably utilized. The probe may also be used to identify a DNA clone corresponding to a full length transcript and a genomic clone or clones that contain the complete gene including regulatory and promotor regions, exons and introns. An example of a screen comprises isolating the coding region of the gene by using the known DNA sequence to synthesize an oligonucleotide probe. Labeled oligonucleotides having a sequence complementary or identical to that of the gene or portion of the gene sequences of the present invention are used to screen a library of genomic DNA to determine which members of the library the probe hybridizes to.

It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product. The probes are thus useful to isolate complementary copies of DNA from other sources or to screen such sources for related sequences.

The present invention further relates to polynucleotides which hybridize to the hereinabove-described sequences if there is at least 70%, preferably at least 90%, and more preferably at least 95% identity between the sequences. (As indicated above, 70% identity would include within such definition a 70 bps fragment taken from a 100 bp polynucleotide, for example.) The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode enzymes which either retain substantially the same biological function or activity as the mature polypeptide encoded by the DNA of FIGS. 1 and 3 (SEQ ID NOS:2 and 4, respectively. In referring to identity in the case of hybridization, as known in the art, such identity refers to complementarity of polynucleotide segments.

Alternatively, the polynucleotide may have at least 15 bases, preferably at least 30 bases, and more preferably at least 50 bases which hybridize to any part of a polynucleotide of the present invention and which has an identity thereto, as hereinabove described, and which may or may not retain activity. For example, such polynucleotides may be employed as probes for the polynucleotides of SEQ ID NOS:1 and 3, for example, for recovery of the polynucleotide or as a diagnostic probe or as a PCR primer.

Thus, the present invention is directed to polynucleotides having at least a 70% identity, preferably at least 90% identity and more preferably at least a 95% identity to a polynucleotide which encodes either the polypeptide of SEQ ID NO:2, or the polypeptide of SEQ ID NO:4, as well as fragments thereof, which fragments have at least 15 bases, preferably at least 30 bases, more preferably at least 50 bases and most preferably fragments having up to at least 150 bases or greater, which fragments are at least 90% identical, preferably at least 95% identical and most preferably at least 97% identical to any portion of a polynucleotide of the present invention.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to polypeptides which have the deduced amino acid sequences of FIGS. 1 and 3 (SEQ ID NOS:2 and 4, respectively) as well as fragments, analogs and derivatives of such polypeptides.

The terms "fragment," "derivative" and "analog" when referring to (a) the polypeptide of FIG. 1 (SEQ ID NO:2) or that encoded by the deposited cDNA, or (b) the polypeptide of FIG. 3 (SEQ ID NO:4), means a polypeptide which either retains substantially the same biological function or activity as such polypeptide, i.e. functions as a G-protein coupled receptor, or retains the ability to bind the ligand or the receptor even though the polypeptide does not function as a G-protein coupled receptor, for example, a soluble form of the receptor.

The polypeptide of the present invention may be a recombinant polypeptide, a natural polypeptide or a synthetic polypeptide, preferably a recombinant polypeptide.

The fragment, derivative or analog of either (a) the polypeptide of FIG. 1 (SEQ ID NO:2) or that encoded by the deposited cDNA, (b) the polypeptide of FIG. 3 (SEQ ID NO:4) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, or (v) one in which a fragment of the polypeptide is soluble, i.e. not membrane bound, yet still binds ligands to the membrane bound receptor. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptides of SEQ ID NOS:2 and 4 (in particular the respective mature polypeptides) as well as polypeptides which have at least 70% similarity (preferably at least a 70% identity) to either the polypeptide of SEQ ID NO:2 or the polypeptide of SEQ ID NO:4 and more preferably at least a 90% similarity (more preferably at least a 90% identity) to the polypeptide of SEQ ID NO:2 or of SEQ ID NO:4 and still more preferably at least a 95% similarity (still more preferably a 90% identity) to the polypeptide of SEQ ID NO:2 or of SEQ ID NO:4 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to a method for identifying and/or isolating cells, tissues, or classes of cells or tissues, by utilizing probes of the polynucleotides that encode the EBI-2 G-protein coupled receptor polypeptide or by utilizing an antibody specific for the EBI-2 G-protein coupled receptor, for example. Since the EBI-2 G-protein coupled receptor polypeptides according to the invention occur in vein endothelial cells, neutrophil leukocyte cells and corpus colosum cells, the above probes or antibodies, for example, may be utilized to identify and/or isolate such cells, tissues or classes of cells or tissues.

The present invention further relates to a method for identifying and/or isolating cells, tissues, or classes of cells or tissues, by utilizing probes of the polynucleotides that encode the EDG-1-like G-protein coupled receptor polypeptide or by utilizing an antibody specific for the EDG-1-like G-protein coupled receptor polypeptide, for example. Since the EDG-1-like G-protein coupled receptor polypeptides according to the invention occur in leukocyte, tonsil, placenta, thymus, lung and pancreas tissue, the above probes or antibodies, for example, may be utilized to identify and/or isolate such cells, tissues or classes of cells or tissues.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the G-protein coupled receptor genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli*. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli*, Streptomyces, *Salmonella typhimurium*; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, PSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The G-protein coupled receptor polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The G-protein coupled receptor of the present invention may be employed in a process for screening for antagonists and/or agonists for the receptor.

In general, such screening procedures involve providing appropriate cells which express the receptor on the surface thereof. In particular, a polynucleotide encoding the receptor of the present invention is employed to transfect cells to thereby express the G-protein coupled receptor. Such transfection may be accomplished by procedures as hereinabove described.

One such screening procedure involves the use of the melanophores which are transfected to express the G-protein coupled receptor of the present invention. Such a screening technique is described in PCT WO 92/01810 published Feb. 6, 1992.

Thus, for example, such assay may be employed for screening for a receptor antagonist by contacting the melanophore cells which encode the G-protein coupled receptor with both the receptor ligand and a compound to be screened. Inhibition of the signal generated by the ligand indicates that a compound is a potential antagonist for the receptor, i.e., inhibits activation of the receptor.

The screen may be employed for determining an agonist by contacting such cells with compounds to be screened and determining whether such compound generates a signal, i.e., activates the receptor.

Other screening techniques include the use of cells which express the G-protein coupled receptor (for example, transfected CHO cells) in a system which measures extracellular pH changes caused by receptor activation, for example, as described in Science, volume 246, pages 181–296 (October 1989). For example, potential agonists or antagonists may be contacted with a cell which expresses the G-protein coupled receptor and a second messenger response, e.g. signal transduction or pH changes, may be measured to determine whether the potential agonist or antagonist is effective.

Another such screening technique involves introducing RNA encoding the G-protein coupled receptor into xenopus oocytes to transiently express the receptor. The receptor oocytes may then be contacted in the case of antagonist screening with the receptor ligand and a compound to be screened, followed by detection of inhibition of a calcium signal.

Another screening technique involves expressing the G-protein coupled receptor in which the receptor is linked to a phospholipase C or D. As representative examples of such cells, there may be mentioned endothelial cells, smooth muscle cells, embryonic kidney cells, etc. The screening for an antagonist or agonist may be accomplished as hereinabove described by detecting activation of the receptor or inhibition of activation of the receptor from the phospholipase second signal.

Another method involves screening for antagonists by determining inhibition of binding of labeled ligand to cells which have the receptor on the surface thereof. Such a method involves transfecting a eukaryotic cell with DNA encoding the G-protein coupled receptor such that the cell expresses the receptor on its surface and contacting the cell with a potential antagonist in the presence of a labeled form of a known ligand. The ligand can be labeled, e.g., by radioactivity. The amount of labeled ligand bound to the receptors is measured, e.g., by measuring radioactivity of the receptors. If the potential antagonist binds to the receptor as determined by a reduction of labeled ligand which binds to the receptors, the binding of labeled ligand to the receptor is inhibited.

The present invention also provides a method for determining whether a ligand not known to be capable of binding to a G-protein coupled receptor can bind to such receptor which comprises contacting a mammalian cell which expresses a G-protein coupled receptor with the ligand under conditions permitting binding of ligands to the G-protein coupled receptor, detecting the presence of a ligand which binds to the receptor and thereby determining whether the ligand binds to the G-protein coupled receptor. The systems hereinabove described for determining agonists and/or antagonists may also be employed for determining ligands which bind to the receptor.

In general, antagonists for G-protein coupled receptors which are determined by screening procedures may be employed for a variety of therapeutic purposes. For example, such antagonists have been employed for treatment of hypertension, angina pectoris, myocardial infarction, ulcers, asthma, allergies, psychoses, depression, migraine, vomiting, stroke, eating disorders, migraine headaches, cancer and benign prostatic hypertrophy.

Agonists for G-protein coupled receptors are also useful for therapeutic purposes, such as the treatment of asthma, Parkinson's disease, acute heart failure, hypotension, urinary retention, and osteoporosis.

Examples of G-protein coupled receptor antagonists include an antibody, or in some cases an oligonucleotide, which binds to the G-protein coupled receptor but does not elicit a second messenger response such that the activity of the G-protein coupled receptor is prevented. Antibodies include anti-idiotypic antibodies which recognize unique determinants generally associated with the antigen-binding site of an antibody. Potential antagonists also include proteins which are closely related to the ligand of the G-protein coupled receptor, i.e. a fragment of the ligand, which have lost biological function and when binding to the G-protein coupled receptor, elicit no response.

A potential antagonist also includes an antisense construct prepared through the use of antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix -see Lee et al., Nucl. Acids Res., 6:3073 (1979); Cooney et al, Science, 241:456 (1988); and Dervan et al., Science, 251: 1360 (1991)), thereby preventing transcription and the production of G-protein coupled receptor. The antisense RNA oligonucleotide hybridizes to the mRNA in vivo and blocks translation of the mRNA molecule into the G-protein coupled receptor (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of G-protein coupled receptor.

Another potential antagonist is a small molecule which binds to the G-protein coupled receptor, making it inaccessible to ligands such that normal biological activity is prevented. Examples of small molecules include but are not limited to small peptides or peptide-like molecules.

Potential antagonists also include a soluble form of a G-protein coupled receptor, e.g. a fragment of the receptor, which binds to the ligand and prevents the ligand from interacting with membrane bound G-protein coupled receptors.

The G-protein coupled receptor and antagonists or agonists may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the topical, intravenous, intraperitoneal, intramuscular, subcutaneous, intranasal or intradermal routes. The pharmaceutical compositions are administered in an amount which is effective for treating and/or prophylaxis of the specific indication. In general, the pharmaceutical compositions will be administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The G-protein coupled receptor polypeptides and antagonists or agonists which are polypeptides, may be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

G-protein coupled receptors are ubiquitous in the mammalian host and are responsible for many biological functions, including many pathologies. Accordingly, it is desirous to find compounds which stimulate a G-protein coupled receptor and compounds which antagonize a G-protein coupled receptor.

This invention further provides a method of identifying compounds which specifically interact with, and bind to, the human G-protein coupled receptors on the surface of a cell which comprises contacting a mammalian cell comprising an isolated DNA molecule encoding the G-protein coupled receptor with a plurality of compounds, determining those which bind to the mammalian cell, and thereby identifying compounds which specifically interact with and bind to a human G-protein coupled receptor of the present invention.

This invention also provides a method of detecting expression of the G-protein coupled receptor on the surface of a cell by detecting the presence of mRNA coding for a G-protein coupled receptor which comprises obtaining total mRNA from the cell and contacting the mRNA so obtained with a nucleic acid probe comprising a nucleic acid molecule of at least 15 nucleotides capable of specifically hybridizing with a sequence included within the sequence of a nucleic acid molecule encoding a human G-protein coupled receptor under hybridizing conditions, detecting the presence of mRNA hybridized to the probe, and thereby detecting the expression of the G-protein coupled receptor by the cell.

This invention is also related to the use of the G-protein coupled receptor gene as part of a diagnostic assay for detecting diseases or susceptibility to diseases related to the presence of mutated G-protein coupled receptor genes. Such diseases are related to cell transformation, such as tumors and cancers.

Individuals carrying mutations in the human G-protein coupled receptor gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding the G-protein coupled receptor protein can be used to identify and analyze G-protein coupled receptor mutations. For example, deletions and insertions can be detected by a change in size of the amplified product in comparison to the normal genotype. Point mutations can be identified by hybridizing amplified DNA to radiolabeled G-protein coupled receptor RNA or alternatively, radiolabeled G-protein coupled receptor antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of soluble forms of the receptor polypeptides of the present invention in various tissues. Assays used to detect levels of the soluble receptor polypeptides in a sample derived from a host are well known to those of skill in the art and include radioimmunoassays, competitive-binding assays, Western blot analysis and preferably as ELISA assay.

An ELISA assay initially comprises preparing an antibody specific to antigens of the G-protein coupled receptor polypeptides, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any G-protein coupled receptor proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to G-protein receptor proteins. Unattached reporter antibody is then washed out. Peroxidase substrates are then added to the dish and the amount of color developed in a given time period is a measurement of the amount of G-protein coupled receptor proteins present in a given volume of patient sample when compared against a standard curve.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 μg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of EBI-2

The DNA sequence encoding EBI-2, ATCC # 209003, is initially amplified using PCR oligonucleotide primers corresponding to the 5' sequences of the processed EBI-2 protein (minus the signal peptide sequence) and the vector sequences 3' to the EBI-2 gene. Additional nucleotides corresponding to EBI-2 were added to the 5' and 3' sequences respectively. The 5' oligonucleotide primer has the sequence 5' CCGAGGATCCATGCAAGCCGTCGA-CAAT 3' (SEQ ID NO:5) contains a BamHI restriction enzyme site followed by 18 nucleotides of the EBI-2 coding sequence starting from the presumed terminal amino acid of the processed protein codon. The 3' sequence 5' CCGAG-GATCCTTACATTGGAGTCTCTTC 3' (SEQ ID NO:6) contains complementary sequences to BamHI site and is followed by 18 nucleotides of EBI-2. The restriction enzyme sites correspond to the restriction enzyme sites on the bacterial expression vector pQE-60. (Qiagen, Inc., Chatsworth, Calif., 91311). pQE-60 encodes antibiotic resistance ($Amp^r$), a bacterial origin of replication (ori), an IPTG-regulatable promoter operator (P/O), a ribosome binding site (RBS), a 6-His tag and restriction enzyme sites. pQE-60 was then digested with BamhI. The amplified sequences were ligated into pQE-60 and were inserted in frame with the sequence encoding for the histidine tag and the RBS. The ligation mixture was then used to transform E. coli strain M15/rep 4 (Qiagen, Inc.) by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance ($Kan^r$). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 ($O.D.^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized hSca-2 was purified from this solution by chromatography on a Nickel-Chelate column under conditions that allow for tight binding by proteins containing the 6-His tag (Hochuli, E. et al., J. Chromatography 411:177–184 (1984)). hSca-2 (95% pure was eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate.

EXAMPLE 2

Cloning and Expression of EBI-2 Using the Baculovirus Expression System

The DNA sequence encoding the full length EBI-2 protein, ATCC # 209003, was amplified Using PCR oligonucleotide primers corresponding to the 5' and 3' sequences of the gene:

The 5' primer has the sequence 5' CCGAGGATCCGC-CATC ATGCAAGCCGCGACAAT (SEQ ID NO:7) and contains a BamHI restriction enzyme site (in bold) followed by 6 nucleotides resembling an efficient signal for the initiation of translation in eukaryotic cells (Kozak, M., J. Mol. Biol., 196:947–950 (1987) which is just behind the first 18 nucleotides of the EBI-2 gene (the initiation codon for translation "ATG" is underlined).

The 3' primer has the sequence 5' CCGAGGATCCTTA-CATTGGAGTCTCTTC 3' (SEQ ID NO:8) and contains the cleavage site for the restriction endonuclease BamHI and 18 nucleotides complementary to the 3' translated sequence of the extracellular part of EBI-2. The amplified sequences were isolated from a 1% agarose gel using a commercially available kit ("Geneclean," BIO 101 Inc., La Jolla, Calif.). The fragment was then digested with the endonucleases BamHI, and purified again on a 1% agarose gel. This fragment is designated F2.

The vector pA2 (modification of pVL941 vector, discussed below) is used for the expression of the EBI-2 protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases BamHI. The polyadenylation site of the simian virus (SV)40 is used for efficient polyadenylation. For an easy selection of recombinant virus the beta-galactosidase gene from E.coli is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pA2 such as pRG1 and pA2-GP in which case the 5' primer are changed accordingly, and pAc373, pVL941 and pAcIM1 (Luckow, V. A. and Summers, M. D., Virology, 170:31–39).

The plasmid was digested with the restriction enzyme BamHI and then dephosphorylated using calf intestinal phosphatase by procedures known in the art. The DNA was then isolated from a 1% agarose gel using the commercially available kit ("Geneclean" BIO 101 Inc., La Jolla, Calif.). This vector DNA is designated V2.

Fragment F2 and the dephosphorylated plasmid V2 were ligated with T4 DNA ligase. E.coli HB101 cells were then transformed and bacteria identified that contained the plasmid (pBacEBI-2) with the EBI-2 gene using the enzyme BamHI. The sequence of the cloned fragment was confirmed by DNA sequencing.

5 μg of the plasmid pBacEBI-2 was co-transfected with 1.0 μg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 μg of BaculoGold™ virus DNA and 5 μg of the plasmid pBacEBI-2 were mixed in a sterile well of a microtiter plate containing 50 μl of serum free Grace's medium (Life Technologies Inc., Gaithersburg, Md.). Afterwards 10 μl Lipofectin plus 90 μl Grace's medium were added, mixed and incubated for 15 minutes at room temperature. Then the transfection mixture was added drop-wise to the Sf9 insect cells (ATCC CRL 1711) seeded in a 35 mm tissue culture plate with 1 ml Grace's medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue-gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the virus was added to the cells and blue stained plaques were picked with the tip of an Eppendorf pipette. The agar containing the recombinant viruses was then resuspended in an Eppendorf tube containing 200 μl of Grace's medium. The agar was removed by a brief centrifugation and the supernatant containing the recombinant baculovirus was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-EBI-2 at a multiplicity of infection (MOI) of 2. Six hours later the medium was removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) were added. The cells were further incubated for 16 hours before they were harvested by centrifugation and the labelled proteins visualized by SDS-PAGE and autoradiography.

EXAMPLE 3

Expression of Recombinant EBI-2 in COS Cells

The expression of plasmid, EBI-2 HA is derived from a vector pcDNAI/Amp (Invitrogen) containing: 1) SV40 origin of replication, 2) ampicillin resistance gene, 3) *E.coli* replication origin, 4) CMV promoter followed by a polylinker region, an SV40 intron and polyadenylation site. A DNA fragment encoding the entire EBI-2 precursor and a HA tag fused in frame to its 3' end was cloned into the polylinker region of the vector, therefore, the recombinant protein expression is directed under the CMV promoter. The HA tag corresponds to an epitope derived from the influenza hemagglutinin protein as previously described (I. Wilson, H. Niman, R. Heighten, A Cherenson, M. Connolly, and R. Lerner, 1984, Cell 37:767, (1984)). The infusion of HA tag to the target protein allows easy detection of the recombinant protein with an antibody that recognizes the HA epitope.

The plasmid construction strategy is described as follows:

The DNA sequence encoding EBI-2, ATCC # 209003, was constructed by PCR using two primers: the 5' primer 5' CCGAGGATCCGCCATCATGCAAGCCGTCGACAAT 3' (SEQ ID NO:9) contains a BamHI site followed by EBI-2 coding sequence starting from the initiation codon; the 3' sequence 5' CCGATCTAGATTAATCCCATACGACGTC-CCAGACTACGCTCATGGAGTCTCTTC 3' (SEQ ID NO:10) contains complementary sequences to XbaI site, translation stop codon, HA tag and EBI-2 coding sequence (not including the stop codon). Therefore, the PCR product contains a BamHI site, EBI-2 coding sequence followed by HA tag fused in frame, a translation termination stop codon next to the HA tag, and an XbaI site. The PCR amplified DNA fragment and the vector, pcDNAI/Amp, were digested with BamHI and XbaI restriction enzyme and ligated. The ligation mixture was transformed into *E. coli* strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant EBI-2 COS cells were transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the EBI-2 HA protein was detected by radiolabelling and immunoprecipitation method (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media was then collected and cells were lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media were precipitated with an HA specific monoclonal antibody. Proteins precipitated were analyzed on 15% SDS-PAGE gels.

EXAMPLE 4

Expression Via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

EXAMPLE 5

Bacterial Expression and Purification of EDG-1-Like Polypeptide

The DNA sequence encoding EDG-1-like polypeptide, ATCC # 209004, is initially amplified using PCR oligonucleotide primers corresponding to the 5' sequences of the processed EDG-1-like polypeptide protein (minus the signal peptide sequence) and the vector sequences 3' to the EDG-1-like polypeptide gene. Additional nucleotides corresponding to EBI-2 were added to the 5' and 3' sequences respectively. The 5' oligonucleotide primer has the sequence 5' CCGAGGATCCATGAACGCCACGGGGACC 3' (SEQ ID NO:11) contains a BamHI restriction enzyme site followed by 18 nucleotides of the EDG-1-like polypeptide coding sequence starting from the presumed terminal amino acid of the processed protein codon. The 3' sequence 5' CCGAGGATCCTCAGATGCTCCGCACGCT 3' (SEQ ID NO:12) contains complementary sequences to BamHI site and is followed by 18 nucleotides of EDG-1-like polypeptide. The restriction enzyme sites correspond to the restriction enzyme sites on the bacterial expression vector pQE-60. (Qiagen, Inc., Chatsworth, Calif., 91311). pQE-60 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-60 was then digested with BamhI. The amplified sequences were ligated into pQE-60 and were inserted in frame with the sequence encoding for the histidine tag and the RBS. The ligation mixture was then used to transform E. coli strain M15/rep 4 (Qiagen, Inc.) by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized EBI-2 was purified from this solution by chromatography on a Nickel-Chelate column under conditions that allow for tight binding by proteins containing the 6-His tag (Hochuli, E. et al., J. Chromatography 411:177–184 (1984)). EBI-2 (95% pure was eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate.

EXAMPLE 6

Cloning and Expression of EDG-1-like Polypeptide Using the Baculovirus Expression System The DNA sequence encoding the full length EDG-1-like polypeptide protein, ATCC # 209004, was amplified using PCR oligonucleotide primers corresponding to the 5' and 3' sequences of the gene:

The 5' primer has the sequence 5' GCGAGGATCCGC-CATCATGAACGCCACGGGGACC 3' (SEQ ID NO:13) and contains a BamHI restriction enzyme site (in bold) followed by 6 nucleotides resembling an efficient signal for the initiation of translation in eukaryotic cells (Kozak, M., J. Mol. Biol., 196:947–950 (1987) which is just behind the first 18 nucleotides of the EDG-1-like polypeptide gene (the initiation codon for translation "ATG" is underlined).

The 3' primer has the sequence 5' CCGAGGATCCTCA-GATGCTCCGCACGCT 3' (SEQ ID NO:14) and contains the cleavage site for the restriction endonuclease BamHI and 18 nucleotides complementary to the 3' translated sequence of the extracellular part of EDG-1-like polypeptide. The amplified sequences were isolated from a 1% agarose gel using a commercially available kit ("Geneclean," BIO 101 Inc., La Jolla, Calif.). The fragment was then digested with the endonucleases BamHI, and purified again on a 1% agarose gel. This fragment is designated F2.

The vector pA2 (modification of pVL941 vector, discussed below) is used for the expression of the EDG-1-like polypeptide protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases BamHI. The polyadenylation site of the simian virus (SV)40 is used for efficient polyadenylation. For an easy selection of recombinant virus the beta-galactosidase gene from E.coli is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pA2 such as pRG1 and pA2-GP in which case the 5' primer are changed accordingly, and pAc373, pVL941 and pAcIM1 (Luckow, V. A. and Summers, M. D., Virology, 170:31–39).

The plasmid was digested with the restriction enzyme BamHI and then dephosphorylated using calf intestinal phosphatase by procedures known in the art. The DNA was then isolated from a 1% agarose gel using the commercially available kit ("Geneclean" BIO 101 Inc., La Jolla, Calif.). This vector DNA is designated V2.

Fragment F2 and the dephosphorylated plasmid V2 were ligated with T4 DNA ligase. E.coli HB101 cells were then transformed and bacteria identified that contained the plasmid (pBacEDG-1-like polypeptide) with the EDG-1-like polypeptide gene using the enzyme BamHI. The sequence of the cloned fragment was confirmed by DNA sequencing.

5 µg of the plasmid pBacEDG-1-like polypeptide was co-transfected with 1.0 µg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 µg of BaculoGold™ virus DNA and 5 µg of the plasmid pBacEDG-1-like polypeptide were mixed in a sterile well of a microtiter plate containing 50 µl of serum free Grace's medium (Life Technologies Inc., Gaithersburg, Md.). Afterwards 10 µl Lipofectin plus 90 µl Grace's medium were added, mixed and incubated for 15 minutes at room temperature. Then the transfection mixture was added drop-wise to the Sf9 insect cells (ATCC CRL 1711) seeded in a 35 mm tissue culture plate with 1 ml Grace's medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue-gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the virus was added to the cells and blue stained plaques were picked with the tip of an Eppendorf pipette. The agar containing the recombinant viruses was then resuspended in an Eppendorf tube containing 200 µl of Grace's medium. The agar was removed by a brief centrifugation and the supernatant containing the recombinant baculovirus was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-EDG-1-like polypeptide at a multiplicity of infection (MOI) of 2. Six hours later the medium was removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) were added. The cells were further incubated for 16 hours before they were harvested by centrifugation and the labelled proteins visualized by SDS-PAGE and autoradiography.

EXAMPLE 7

Expression of Recombinant EDG-1-like Polypeptide in COS Cells

The expression of plasmid, EDG-1-like polypeptide HA is derived from a vector pcDNAI/Amp (Invitrogen) containing: 1) SV40 origin of replication, 2) ampicillin resistance gene, 3) E.coli replication origin, 4) CMV promoter followed by a polylinker region, an SV40 intron and polyadenylation site. A DNA fragment encoding the entire EDG-1-like polypeptide precursor and a HA tag fused in frame to its 3' end was cloned into the polylinker region of the vector, therefore, the recombinant protein expression is directed under the CMV promoter. The HA tag corresponds to an epitope derived from the influenza hemagglutinin protein as previously described (I. Wilson, H. Niman, R. Heighten, A Cherenson, M. Connolly, and R. Lerner, 1984, Cell 37:767, (1984)). The infusion of HA tag to the target protein allows easy detection of the recombinant protein with an antibody that recognizes the HA epitope.

The plasmid construction strategy is described as follows:

The DNA sequence encoding EDG-1-like polypeptide, ATCC # 209004, was constructed by PCR using two primers: the 5' primer 5' CCGAGGATCCGCCATCAT-GAACGCCACGGGGACC 3' (SEQ ID NO:15) contains a BamHI site followed by EDG-1-like polypeptide coding sequence starting from the initiation codon; the 3' sequence 5' CCGATCTAGATCAATCCCATACGACGTC-CCAGACTACGCTGATGCTCCGCACGCT 3' (SEQ ID NO:16) contains complementary sequences to XbaI site, translation stop codon, HA tag and EDG-1-like polypeptide coding sequence (not including the stop codon). Therefore, the PCR product contains a BamHI site, EDG-1-like polypeptide coding sequence followed by HA tag fused in frame, a translation termination stop codon next to the HA tag, and an XbaI site. The PCR amplified DNA fragment and the vector, pcDNAI/Amp, were digested with BamHI and XbaI restriction enzyme and ligated. The ligation mixture was transformed into E. coli strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant EDG-1-like polypeptide COS cells were transfected with the expression vector by DEAE-DEXTRAN method (J.

Sambrook, E. Fritsch, T. Maniatis, Molecular Cloning: A Laboratory Manual, Cold Spring Laboratory Press, (1989)). The expression of the EDG-1-like polypeptide HA protein was detected by radiolabelling and immunoprecipitation method (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media was then collected and cells were lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media were precipitated with an HA specific monoclonal antibody. Proteins precipitated were analyzed on 15% SDS-PAGE gels.

EXAMPLE 8

Expression Via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated polynucleotide comprising a nucleic acid encoding amino acids 2 to 384 of SEQ ID NO:4.

2. The isolated polynucleotide of claim 1, which comprises nucleotides 53–1201 of SEQ ID NO:3.

3. The isolated polynucleotide of claim 1, further comprising a heterologous polynucleotide.

4. A composition comprising the isolated polynucleotide of claim 1 and a carrier.

5. An expression vector comprising the isolated polynucleotide of claim 1.

6. A host cell comprising the expression vector of claim 5.

7. A method of producing a polypeptide comprising culturing the host cell of claim 6 under conditions such that said polypeptide is expressed, and recovering said polypeptide.

8. An isolated polypeptide produced by the method of claim 7.

9. The isolated polynucleotide of claim 1, which comprises a nucleic acid encoding amino acids 1 to 384 of SEQ ID NO:4.

10. The isolated polynucleotide of claim 9, which comprises nucleotides 50–1201 of SEQ ID NO:3.

11. The isolated polynucleotide of claim 9, further comprising a heterologous polynucleotide.

12. A composition comprising the isolated polynucleotide of claim 9 and a carrier.

13. An expression vector comprising the isolated polynucleotide of claim 9.

14. A host cell comprising the expression vector of claim 13.

15. A method of producing a polypeptide comprising culturing the host cell of claim 14 under conditions such that said polypeptide is expressed, and recovering said polypeptide.

16. An isolated polypeptide produced by the method of claim 15.

17. An isolated polypeptide comprising amino acids 2 to 384 of SEQ ID NO:4.

18. The isolated polypeptide of claim 17, comprising amino acids 1 to 384 of SEQ ID NO:4.

19. The isolated polypeptide of claim 18, wherein said polypeptide has G-protein coupled receptor activity.

20. The isolated polypeptide of claim 17, further comprising a heterologous polypeptide.

21. A composition comprising the isolated polypeptide of claim 20 and a carrier.

* * * * *

UNITED STATES PATENT AND TRADEMARK OFFICE
CERTIFICATE OF CORRECTION

PATENT NO. : 6,060,272
DATED : May 9, 2000
INVENTOR(S) : Yi Li and Steven M. Ruben It is certified that error appears in the above-identified patent and that said Letters Patent is hereby corrected as shown below:

Column 4,
Line 56, after "20110-2209" please insert a space.

Column 22,
Line 19, please delete the sequence "ATGCAAGCCGCGACAAT" and insert therein -- ATGCAAGCCGTCGACAAT --.

Column 23,
Line 27, please delete "Blue-gal" and insert therein -- Bluo-gal --.

Column 27,
Line 58, delete "Blue-gal" and insert therein -- Bluo-gal --.

Column 48, claim 19
Line 56, please delete "18" and insert therefor -- 17 --.

Column 48, claim 21
Line 61, please delete "20" and insert therefor -- 17 --.

Signed and Sealed this

Twenty-eighth Day of August, 2001

*Attest:*

NICHOLAS P. GODICI
*Attesting Officer*     Acting Director of the United States Patent and Trademark Office